(12) United States Patent
James et al.

(10) Patent No.: US 11,285,090 B2
(45) Date of Patent: Mar. 29, 2022

(54) COSMETIC SKINCARE COMPOSITIONS

(71) Applicant: THE BOOTS COMPANY PLC, Nottingham (GB)

(72) Inventors: Leanne Marie James, Leicestershire (GB); Clare Helena O'Connor, Derbyshire (GB)

(73) Assignee: THE BOOTS COMPANY PLC, Nottingham (GB)

( * ) Notice: Subject to any disclaimer, the term of this patent is extended or adjusted under 35 U.S.C. 154(b) by 131 days.

(21) Appl. No.: 16/490,386

(22) PCT Filed: Feb. 28, 2018

(86) PCT No.: PCT/EP2018/025048
§ 371 (c)(1),
(2) Date: Aug. 30, 2019

(87) PCT Pub. No.: WO2018/171943
PCT Pub. Date: Sep. 27, 2018

(65) Prior Publication Data
US 2021/0196590 A1 Jul. 1, 2021

(30) Foreign Application Priority Data
Mar. 1, 2017 (EP) ..................................... 17020079

(51) Int. Cl.
| | | |
|---|---|---|
| *A61K 36/00* | (2006.01) | |
| *A61K 8/368* | (2006.01) | |
| *A61K 8/9789* | (2017.01) | |
| *A61K 8/31* | (2006.01) | |
| *A61K 8/42* | (2006.01) | |
| *A61K 8/60* | (2006.01) | |
| *A61Q 17/00* | (2006.01) | |
| *A61Q 19/08* | (2006.01) | |

(52) U.S. Cl.
CPC ................ *A61K 8/368* (2013.01); *A61K 8/31* (2013.01); *A61K 8/42* (2013.01); *A61K 8/60* (2013.01); *A61K 8/9789* (2017.08); *A61Q 17/00* (2013.01); *A61Q 19/08* (2013.01); *A61K 2800/522* (2013.01)

(58) Field of Classification Search
CPC ............................... A61Q 19/00; A61Q 19/08
See application file for complete search history.

(56) References Cited

U.S. PATENT DOCUMENTS

2013/0309282 A1\* 11/2013 Takehana ............. A61K 8/0241
424/401
2014/0161849 A1 6/2014 Bickford
2014/0161851 A1 6/2014 Bickford

FOREIGN PATENT DOCUMENTS

| CN | 105125430 A | 12/2015 | |
|---|---|---|---|
| JP | H09291012 A | 11/1997 | |
| WO | WO-2004010958 A2 \* | 2/2004 | ............ A61K 8/922 |
| WO | WO-2013/086518 A1 | 6/2013 | |
| WO | WO-2016/146778 A1 | 9/2016 | |

OTHER PUBLICATIONS

"Ammonium Glycyrrhizate—Technical-Scientific Report", Select Botanical (2014).
"Cucumber Anti-fatigue Eye Mask", Mintel, dated Jul. 6, 2016.
"Daily Oil Free Essence", Mintel, dated Nov. 9, 2012.
"Acnecur Pore Refining Serum with P-Refinyl", Mintel, dated Apr. 11, 2016.
"Bump Fighter", Mintel, dated Jul. 27, 2010.
International Search Report and Written Opinion, corresponding International Application No. PCT/EP2018/025048, dated May 9, 2018.

\* cited by examiner

*Primary Examiner* — Qiuwen Mi
(74) *Attorney, Agent, or Firm* — Marshall, Gerstein & Borun LLP

(57) ABSTRACT

According to the present invention there is provided a cosmetic composition comprising: (i) a salicylic acid compound; (ii) monoammonium glycyrrhizate; and (iii) a polyphenolic antioxidant agent.

10 Claims, 2 Drawing Sheets

Figure 1

Figure 2:
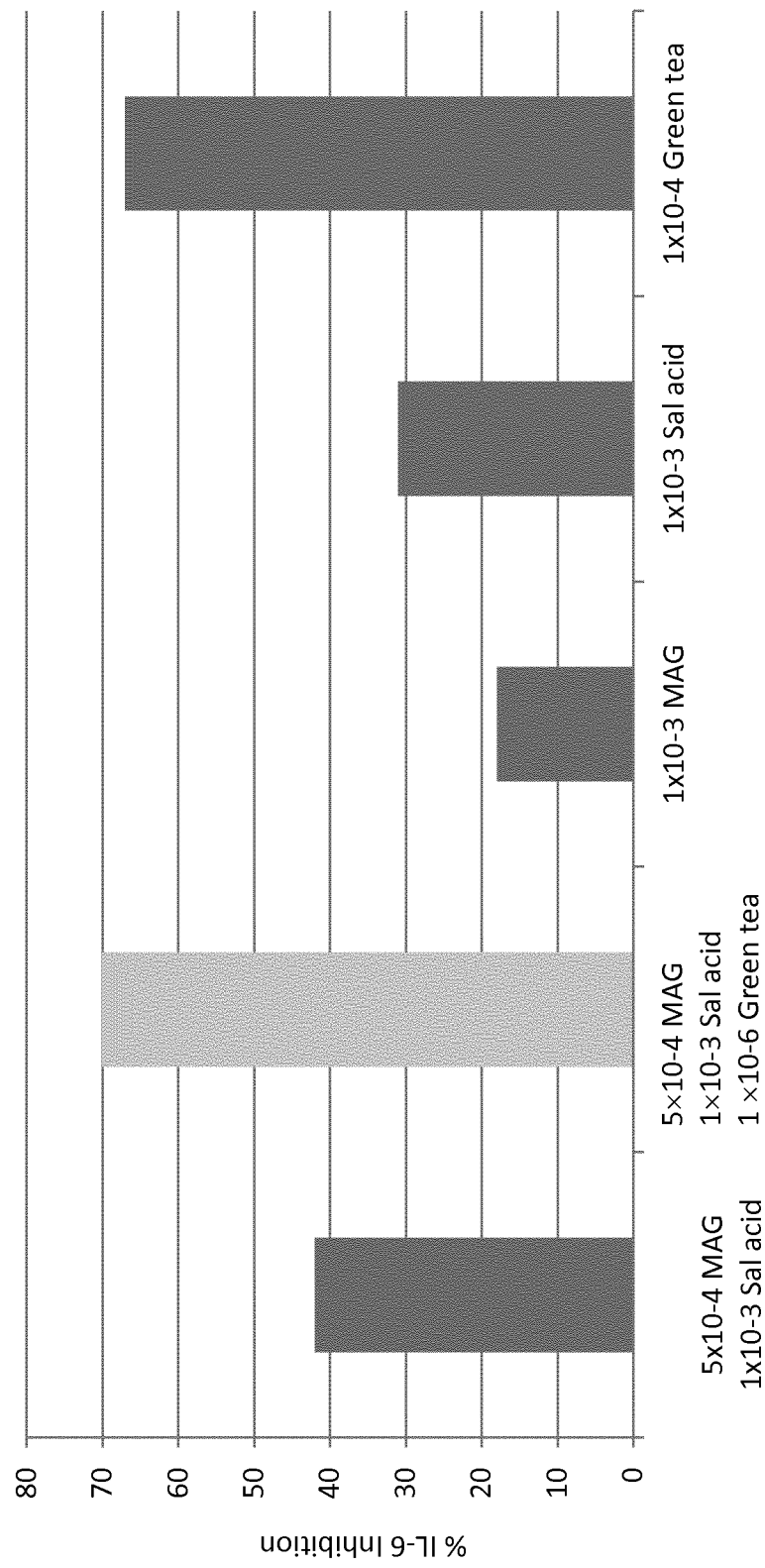

| Material Name | Example formulations (% w/w) | | | | | | | | | |
|---|---|---|---|---|---|---|---|---|---|---|
| | 1 | 2 | 3 | 4 | 5 | 6 | 7 | 8 | 9 | 10 |
| Water | 76.1686 | 55.3234 | 84.95862 | 69.3779 | 57.7699 | 64.8319 | 65.0839 | 64.9394 | 64.9392 | 64.5383 |
| Sequestrene | 0.03 | 0.025 | 0.04 | 0.02 | 0.07 | 0.05 | 0.05 | 0.05 | 0.05 | 0.05 |
| Ethanol | 20 | 40 | 10 | 25 | 35 | 30 | 30 | 30 | 30 | 30 |
| Salicylic acid | 0.6 | 1 | 0.7 | 1.2 | 2.5 | 1.5 | 0.8 | 1.8 | 1 | 0.5 |
| Tween 20 | 0.8 | 0.5 | 0.6 | 0.8 | 1.5 | 1 | 1 | 1 | 1 | 1 |
| Keltrol | 0.8 | 1.5 | 1.8 | 2 | 1.5 | 1 | 1 | 1 | 1 | 1 |
| Monoammonium Glycyrrhizate | 0.7 | 0.8 | 0.3 | 1 | 0.75 | 0.6 | 0.2 | 0.4 | 0.6 | 2 |
| Panthenol | 0 | 0 | 0.7 | 0 | 0 | 0.2 | 0.8 | 0 | 0.5 | 0 |
| Ammonium hydroxide | 0.9 | 0.8 | 0.9 | 0.6 | 0.7 | 0.81 | 0.81 | 0.81 | 0.81 | 0.81 |
| Bisabolol | 0 | 0.05 | 0 | 0 | 0.2 | 0 | 0.25 | 0 | 0.1 | 0.1 |
| Herb ext camellia sinensis leaf | 0.0012 | 0.0015 | 0.0013 | 0.002 | 0.01 | 0.008 | 0.006 | 0.0005 | 0.0007 | 0.0016 |
| Hexylene glycol | 0.0002 | 0.0001 | 0.00008 | 0.0001 | 0.0001 | 0.0001 | 0.0001 | 0.0001 | 0.0001 | 0.0001 |

COSMETIC SKINCARE COMPOSITIONS

FIELD OF THE INVENTION

The present invention relates to cosmetic compositions providing improved skin protection and methods of cosmetic treatment using said compositions.

BACKGROUND OF THE INVENTION

The skin is the first line of defence, serving as a barrier between us and the environment. The skin is a complex organ consisting of three layers: the epidermis, dermis and hypodermis.

The epidermis is the outermost layer, which itself is made up of several layers. The outermost portion of the epidermis, known as the stratum corneum, is relatively waterproof and, when undamaged, prevents most bacteria, viruses, and other foreign substances from entering the body. It also prevents the loss of moisture, heat and other important constituents of the body.

Most of the cells (90-95%) in the epidermis are keratinocytes. They originate from proliferating keratinocyte stem cells in the deepest layer of the epidermis called the basal layer. Resulting keratinocytes further divide and differentiate and slowly migrate up toward the surface of the epidermis as mature cells. Once the keratinocytes reach the stratum corneum at the skin surface they are dead and no longer multiplying and are gradually shed and replaced by newer cells pushed up from below.

The skin is subject to constant attack by a variety of both exogenous and endogenous insults. Exogenous insults include those arising from the environment such as ultraviolet radiation (UVA and UVB), infra-red and visible light, atmospheric pollution (including cigarette smoke) and/or harsh chemicals including surfactants in cosmetic formulations. Such environmental factors may either directly or indirectly result in skin damage by the generation of reactive species and free radicals, for example superoxide anions, hydrogen peroxide, hydroxyl ions, peroxyl ions, ozone, singlet oxygen, sulphur oxide, nitrogen oxide, carbon monoxide, alkoxyl ion, peroxynitrite and heavy metals. Reactive oxygen species (ROS), reactive carbonyl species (RCS) and reactive nitrogen species (RNS) need to be particularly considered. Endogenous insults can also result in skin damage, for example hormonal fluctuations (e.g. cortisol and adrenaline hormones), ageing and other biochemical changes from within the skin.

With respect to atmospheric pollution (including cigarette smoke), polycyclic aromatic hydrocarbons (PAHs) are key pollutants that cause skin damage through a number of different mechanisms including increased melanocyte activation, increased sebum oxidation and mitochondrial damage of keratinocytes and fibroblasts. PAHs can also increase ROS discussed above in the skin.

The process of keratinocyte cell proliferation, differentiation and maturation is vulnerable to the many exogenous and endogenous insults that the skin faces on a daily basis. These insults are known to increase the inflammatory response in the epidermis. One consequence of this inflammation is the increased proliferation of keratinocytes followed by poor maturation and differentiation thereof, resulting in a lower quality stratum corneum and thus skin barrier disruption and/or damage. Once the skin barrier has been disrupted or damaged this further enhances the cascade of inflammation and keratinocyte over proliferation, creating a cycle of unhealthy skin traits. The skin barrier is weakened to the attack of pathogens and toxins, increasing the likelihood of skin redness and irritation, pimples and spots and/or causing the skin to appear dull, dry and scaly.

SUMMARY OF THE INVENTION

The Applicant has identified a consumer need to provide further cosmetic compositions which maintain or improve skin health and/or appearance. The Applicant has found that the compositions of the present invention further provide good and effective benefits to the skin in response to exogenous and endogenous insults.

Accordingly, in a first aspect of the invention there is provided a cosmetic composition comprising:
 (i) a salicylic acid compound;
 (ii) a glycyrrhizic acid compound; and
 (iii) a polyphenolic antioxidant agent.

In another aspect of the invention, there is provided a method of cosmetic treatment of a skin condition comprising the step of applying the cosmetic composition according to the invention onto the skin of a subject afflicted with the skin condition or a risk of being afflicted with the skin condition.

In another aspect of the invention, there is provided a use of the cosmetic composition according to the invention as a topical application on the skin.

It is appreciated that the cosmetic compositions of the present invention can be effective in treating skin damage as a result of pollution insult or preventing the detrimental effects of pollution insult to the skin. Thus, a further aspect of the present invention provides a method of cosmetically treating skin damage as a result of pollution insult, or of cosmetically preventing the detrimental effects of pollution to the skin, said method comprising applying an effective amount of cosmetic composition defined above to the skin.

DETAILED DESCRIPTION OF THE INVENTION

The invention makes use of a salicylic compound. The salicylic acid compound may be salicylic acid (i.e. 2-hydroxybenzoic acid) or a derivative thereof. The derivative may be in the form of a salt of salicylic acid such as a metal salt or ammonium salt. For example, a sodium, potassium, ammonium, triethanolammonium, glucammonium, copper, titanium, or zinc salt of salicylic acid. Other derivatives of salicylic acid include benzyl salicylate, betaine salicylate, thiosalicylic acid and salicylic acid esters, such as alkyl esters of C1-C20. In one embodiment, the salicylic acid compound is salicylic acid.

The salicylic acid compound may be present in an amount of from about 0.01% to about 10% by weight of the composition (i.e. w/w), e.g. in an amount of about 0.01% to about 7% by weight of the composition, about 0.05% to about 6% by weight of the composition, about 0.05% to about 5% by weight of the composition, about 0.1 to about 5% by weight of the composition. In one embodiment, the salicylic acid compound is present in an amount of about 0.1% to about 3% by weight of the composition.

The invention makes use of a glycyrrhizic acid compound. The glycyrrhizic acid compound may be glycyrrhizic acid or a derivative thereof. The derivative may be in the form of a salt of glycyrrhizic acid such as monoammonium glycyrrhizate (MAG), triammonium glycyrrhizate, monopotassium glycyrrhizate, dipotassium glycyrrhizate, tripotassium glycyrrhizate, monosodium glycyrrhizate, disodium glycyrrhizate, trisodium glycyrrhizate, or combinations thereof. In one embodiment, the glycyrrhizic acid compound is selected from the group consisting of monoammonium glycyrrhizate (MAG), triammonium glycyrrhizate, monopotassium glycyrrhizate, dipotassium glycyrrhizate, tripotassium glycyrrhizate, monosodium glycyrrhizate, disodium glycyrrhizate, trisodium glycyrrhizate, and combinations thereof. In one embodiment, the glycyrrhizic acid compound is selected from the group of monoammonium glycyrrhizate (MAG), dipotassium glycyrrhizate, disodium glycyrrhizate, trisodium glycyrrhizate, and combinations thereof. In one embodiment, the glycyrrhizic acid compound comprises monoammonium glycyrrhizate (MAG), i.e. in one aspect the present invention provides a cosmetic composition comprising: (i) a salicylic acid compound; (ii) monoammonium glycyrrhizate; and (iii) a polyphenolic antioxidant agent.

The glycyrrhizic acid compound (e.g. the MAG) may be present in an amount of about 0.001% to about 10% by weight of the composition (i.e. w/w), in an amount of about 0.01% to about 10% by weight of the composition, about 0.01% to about 5% by weight of the composition, about 0.01% to about 3% by weight of the composition, about 0.01 to about 2% by weight of the composition. In one embodiment, glycyrrhizic acid compound (e.g. the MAG) is present in an amount of about 0.05% to about 5% by weight of the composition.

The invention makes use of a polyphenolic antioxidant agent. The term "polyphenolic" can be defined as a compound which possesses aromatic rings bearing one or more hydroxy substituents, including functional derivatives.

The term "polyphenolic antioxidant agent" is intended to mean a plant, algal or fungal extract, or derivative thereof, comprising one or more species which provide an antioxidant benefit, such as flavonoid species; phenolic acid species; stilbene species; lignin species, or combinations thereof.

In one embodiment the polyphenolic antioxidant agent comprises one or more flavonoid species. Flavonoid species include flavones, flavonols, flavanones, flavanols, anthocyanidins, anthocyanins, proanthocyanidins, flavans, isoflavones and isoflavonoids. Some specific examples of flavonoid species are catechins (catechin, epicatechin, gallocatechin, epigallocatechin, epicatechin gallate, epigallocatechin gallate), quercetin, rutin, hesperidin and genistein.

Plants provide a rich and cheap source of polyphenolic antioxidant agents, and are therefore an efficient source of said agents. Naturally occurring polyphenolic antioxidant agents may therefore be used.

However, the same or similar actives can be also prepared synthetically. The term "polyphenolic antioxidant agent" is therefore intended to cover synthetic polyphenols, such as synthetic analogues of naturally occurring polyphenolic antioxidant agents. Thus chemically synthesized or purified polyphenols and mixtures thereof may be used in place of plant extracts. Polyphenols may be synthesized or extracted from natural sources by any suitable method known to those skilled in the art, particularly using food-grade solvents. Liquid and solid (e.g. granulate or powder form) extracts are suitable.

Extracts (e.g. aqueous or alcoholic) can be obtained from plant parts including but not limited to leaves, raw or cooked whole fruit, berries and vegetables, nuts, the skins of fruit, fruit flesh, fruit rind, peel, pips, cones (e.g. hops), seeds or stones, bark, buds, flowers or parts thereof, including petals and pollen, roots, rhizomes and tubers, and stems. The plant extract may be selected from the group consisting of essential oils, extracts from leaves, extracts from stems, extracts from petals, extracts from seeds, extracts from roots, extracts from pollen, and combinations thereof. In one embodiment, extracts (e.g. lyophilised extracts) from leaves are used.

The term "polyphenolic antioxidant agent" is intended to mean a plant extract or derivative thereof comprising flavonoid species, including flavones, flavonols, flavanones, flavanols, anthrocyanidins and isoflavonoids; phenoic acid species; stilbenes; lignans or combinations thereof, which provides an antioxidant benefit. Plants provide a rich and cheap source of polyphenolic antioxidant agents, and are therefore an efficient source of said agents. Similar actives can be also prepared synthetically and as such are analogues. The term "polyphenolic antioxidant agent" is also intended to cover said analogues. The plant extract may be selected from the group consisting of essential oils, extracts from leaves, extracts from stems, extracts from petals, extracts from seeds, extracts from roots, extracts from pollen, and combinations thereof.

The polyphenolic antioxidant agent may be selected from the group consisting of extracts of: green tea (e.g. green leaves of *Camellia sinensis*), mulberry (e.g. *Morus alba*), ginseng (e.g. *Panax ginseng*), raspberry, oregano (e.g. *Origanum vulgare*), white tea (e.g. *Camellia sinensis*), red tea, Mohani tea, black tea, Oolong tea, yellow tea, jasmine tea, Pu Erh tea, blueberry (e.g. *Vaccinium cyanococcus*), French maritime pine bark (e.g. *Pinus pinaster*, sold under the trade name of Pycnogenol), rosemary (e.g. *Rosmarinus officialis*), grape, including grape seed (e.g. *Vitis vinifera*), fennel (e.g. *Foeniculi fructus*), *Caragana sinica*, majoram (e.g. *Origanum majorana*), crocus (e.g. *Crocus sativus*), apple (e.g. *Malus domestica*), coffee, green coffee, cherry (e.g. *Prunus avium*), snow algae (e.g. *Chlamydomonas nivalis*), Emblica (e.g. *Pyllanthus emblica*), ginkgo (e.g. *Ginkgo biloba*), moringa (e.g. *Moringa oleilera*), ginger, magnolia (e.g. *Magnolioideae virginiana*), French saffron, edelweiss (e.g. *Leontopodium alpinium*), white lotus (e.g. nymphaea alba), turmeric root, marshmallow (e.g. *Althaea officianlis*), burdock (e.g. *Arctium lappa*), bilberry (e.g. *Vaccinium myrtillus*), cranberry (e.g. *Vaccinium oxycoccus*), pomegranate (e.g. *Punica granatum*), sage (e.g. *Salvia officianlis*), thyme (e.g. *Thymus vulgaris*), sunflower (e.g. *Helianthus annus*), wild carrot (e.g. *Daucus carota*), hop (e.g. *Humulus lupulus*), witch hazel (e.g. *Hamamelis*), oak (e.g. *Quercus*), Camellia (e.g. *Theacea*), red clover (e.g. *Tritolium pratense*), flax (e.g. *Linium usitatissiumum*), lemon (e.g. *Citrus limon*), birch (e.g. *Betula*), cornflower (e.g. *Centaurea cyanus*), geranium, polygonum, soy (e.g. *Glycine max*), Sophora (e.g. *Sophora flavescens*), and combinations thereof.

In one embodiment, the polyphenolic antioxidant agent is selected from the group consisting of extracts of: green tea (e.g. green leaves of *C. sinensis*), white tea (e.g. *C. sinensis*), red tea, Mohani tea, black tea, Oolong tea, yellow tea, jasmine tea, Pu Erh tea, mulberry (e.g. *M. alba*), ginseng (e.g. *P. ginseng*), rosemary (e.g. *R. officialis*), blueberry (e.g. *V. cyanococcus*), apple (e.g. *M. domestica*), cherry (e.g. *P. avium*), Emblica (e.g. *P. emblica*), ginkgo (e.g. *G. biloba*), moringa (e.g. *M. oleilera*), white lotus (e.g. nymphaea alba), marshmallow (e.g. *A. officianlis*), bilberry (e.g. *V. myrtillus*), cranberry (e.g. *V. oxycoccus*), pomegranate (e.g. *P. granatum*), thyme (e.g. *T. vulgaris*), cornflower (e.g. *C. cyanus*), geranium, polygonum, soy (e.g. *G. max*), Sophora (e.g. *S. flavescens*), burdock (e.g. *A. lappa*) and combinations thereof.

In one embodiment, the polyphenolic antioxidant agent is selected from the group consisting of extracts of: green tea (e.g. *C. sinensis*), ginkgo (e.g. *G. biloba*), Emblica (e.g. *P.*

*emblica*), mulberry (e.g. *M. alba*), ginseng (e.g. *P. ginseng*), Sophora (e.g. *S. flavescens*), and combinations thereof.

In one embodiment, the polyphenolic antioxidant agent comprises an extract of green tea. The extract of green tea may be an extract from the leaves, stems, seeds, petals, pollen and/or roots of a green tea plant (e.g. *C. sinensis*). The extract of green tea may be an essential oil. In one embodiment, the extract of green tea is an extract from the leaves of a green tea plant.

The polyphenolic antioxidant agent may be present in an amount of about 0.0001% to about 20% by weight of the composition (i.e. w/w), about 0.0001% to about 15% by weight of the composition, about 0.0001% to about 10% by weight of the composition, about 0.0001% to about 5% by weight of the composition, about 0.0001 to about 2% by weight of the composition. In one embodiment, the polyphenolic antioxidant agent is present in an amount of about 0.0005% to about 3% by weight of the composition.

The cosmetic composition of the invention may further comprise panthenol or α-bisabolol. The cosmetic composition of the invention may further comprise panthenol. The cosmetic composition of the invention may further comprise α-bisabolol. The cosmetic composition of the invention may further comprise panthenol and α-bisabolol.

In one embodiment, the combination of the salicylic acid compound, the glycyrrhizic acid compound (e.g. MAG) and the green tea may be surprisingly more effective in protecting the skin from exogenous and endogenous insults than the individual agents alone.

The cosmetic composition of the invention may comprise the salicylic acid compound in an amount about 20 times or less the amount of the glycyrrhizic acid compound (e.g. MAG). For example, about 19 times or less, about 18 times or less, about 17 times or less, about 16 times or less, about 15 times or less, about 14 times or less, about 15 times or less, about 14 times or less, about 13 times or less, about 12 times or less, about 11 times or less, about 10 times or less, about 9.5 times or less, about 9 times or less, about 8.5 times or less, about 8 times or less, about 7.5 times or less, about 7 times or less, about 6.5 times or less, about 6 times or less, about 5.5 times or less, about 5 times or less, about 4.5 times or less, about 4 times or less, about 3.5 times or less, about 3 times or less, about 2.5 times or less, about 2 times or less, or about 1.5 times or less.

The cosmetic composition of the invention may comprise the salicylic acid compound in an amount at least about 10 times as much as the amount of the polyphenolic antioxidant agent. For example, at least about 20 times as much, at least about 50 times as much, at least about 100 times as much, at least about 200 times as much, at least about 300 times as much, at least about 400 times as much, or at least about 500 times as much.

The cosmetic composition of the invention may comprise the glycyrrhizic acid compound (e.g. MAG) in an amount at least about 10 times as much as the amount of the polyphenolic antioxidant agent. For example, at least about 20 times as much, at least about 50 times as much, at least about 80 times as much, at least about 100 times as much, at least about 150 times as much, at least about 200 times as much, or at least about 250 times as much.

The cosmetic composition of the invention may comprise the salicylic acid compound, the glycyrrhizic acid compound (e.g. MAG), and the polyphenolic antioxidant agent in an amount of about 0.01% to about 20%, 0.01% to about 10%, about 0.01% to about 5%, about 0.01% to about 3%, about 0.1% to about 10%, about 0.1% to about 5%, about 0.1% to about 3%, or about 0.5% to about 5% by weight of the composition (i.e. w/w). In one embodiment, the cosmetic composition of the invention comprises the salicylic acid compound, the glycyrrhizic acid compound (e.g. MAG), and the extract of green tea in an amount of about 0.5% to about 3% by weight of the composition.

The cosmetic composition of the invention may comprise the salicylic acid compound in an amount of about 0.01% to about 10%, about 0.01% to about 5%, about 0.05% to about 5%, about 0.05% to about 3%, or about 0.1% to about 5% by weight of the composition, the glycyrrhizic acid compound (e.g. MAG) in an amount of about 0.01% to about 10%, about 0.01% to about 5%, about 0.01% to about 2%, about 0.05% to about 3%, or about 0.05% to about 2% by weight of the composition and the polyphenolic antioxidant agent in an amount of about 0.0001% to about 10%, about 0.0001% to about 5%, about 0.0001% to about 2%, about 0.0005% to about 3%, or about 0.001% to about 2% by weight of the composition. In one embodiment, the cosmetic composition of the invention may comprise the salicylic acid compound in an amount of about 0.01% to about 10% by weight of the composition, the glycyrrhizic acid compound (e.g. MAG) in an amount of about 0.01% to about 10% by weight of the composition and the extract of green tea in an amount of about 0.01% to about 10% by weight of the composition.

In one embodiment, the cosmetic composition of the invention comprises:
(i) a salicylic acid compound selected from the group consisting of salicylic acid and derivatives thereof;
(ii) a glycyrrhizic acid compound selected from the group consisting of glycyrrhizic acid or a derivative thereof (e.g. MAG); and
(iii) a polyphenolic antioxidant agent selected from the group consisting of extracts of: green tea (e.g. green leaves of *C. sinensis*), mulberry (e.g. *M. alba*), ginseng (e.g. *P. ginseng*), raspberry, oregano (e.g. *O. vulgare*), white tea (e.g. *C. sinensis*), red tea, Mohani tea, black tea, Oolong tea, yellow tea, jasmine tea, Pu Erh tea, blueberry (e.g. *V. cyanococcus*), French maritime pine bark (e.g. *P. pinaster*, sold under the trade name of Pycnogenol), rosemary (e.g. *R. officialis*), grape, including grape seed (e.g. *V. vinifera*), fennel (e.g. *F. fructus*), *C. sinica*, majaoram (e.g. *O. majorana*), crocus (e.g. *C. sativus*), apple (e.g. *M. domestica*), coffee, green coffee, cherry (e.g. *P. avium*), snow algae (e.g. *C. nivalis*), Emblica (e.g. *P. emblica*), ginkgo (e.g. *G. biloba*), moringa (e.g. *M. oleilera*), ginger, magnolia (e.g. *M. virginiana*), French saffron, edelweiss (e.g. *L. alpinium*), white lotus (e.g. *N. alba*), turmeric root, marshmallow (e.g. *A. officianlis*), burdock (e.g. *A. lappa*), bilberry (e.g. *V. myrtillus*), cranberry (e.g. *V. oxycoccus*), pomegranate (e.g. *P. granatum*), sage (e.g. *S. officianlis*), thyme (e.g. *T. vulgaris*), sunflower (e.g. *H. annus*), wild carrot (e.g. *D. carota*), hop (e.g. *H. lupulus*), witch hazel (e.g. *Hamamelis*), oak (e.g. *Quercus*), Camellia (e.g. *Theacea*), red clover (e.g. *T. pratense*), flax (e.g. *L. usitatissiumum*), lemon (e.g. *C. limon*), birch (e.g. *Betula*), cornflower (e.g. *C. cyanus*), geranium, polygonum, soy (e.g. *G. max*), Sophora (e.g. *S. flavescens*), and combinations thereof.

In one embodiment, the cosmetic composition of the invention comprises:
(i) a salicylic acid compound selected from the group consisting of salicylic acid and derivatives thereof;
(ii) a glycyrrhizic acid compound selected from the group consisting of glycyrrhizic acid or a derivative thereof (e.g. MAG); and (iii) a polyphenolic antioxidant agent selected from the group consisting of extracts of: green tea (e.g. green leaves of *C. sinensis*), mulberry (e.g. *M. alba*), ginseng (e.g. *P. ginseng*), raspberry, oregano (e.g. *O. vulgare*), white tea (e.g. *C. sinensis*), red tea, Mohani tea, black tea, Oolong tea, yellow tea, jasmine tea, Pu Erh tea, blueberry (e.g. *V. cyanococcus*), French maritime pine bark (e.g. *P. pinaster*, sold under the trade name of Pycnogenol), rosemary (e.g. *R. officialis*), grape, including grape seed (e.g. *V. vinifera*), fennel (e.g. *F. fructus*), *C. sinica*, majaoram (e.g. *O. majorana*), crocus (e.g. *C. sativus*), apple (e.g. *M. domestica*), coffee, green coffee, cherry (e.g. *P. avium*), snow algae (e.g. *C. nivalis*), Emblica (e.g. *P. emblica*), ginkgo (e.g. *G. biloba*), moringa (e.g. *M. oleilera*), ginger, magnolia (e.g. *M. virginiana*), French saffron, edelweiss (e.g. *L. alpinium*), white lotus (e.g. *N. alba*), turmeric root, marshmallow (e.g. *A. officianlis*), burdock (e.g. *A. lappa*), bilberry (e.g. *V. myrtillus*), cranberry (e.g. *V. oxycoccus*), pomegranate (e.g. *P. granatum*), sage (e.g. *S. officianlis*), thyme (e.g. *T. vulgaris*), sunflower (e.g. *H. annus*), wild carrot (e.g. *D. carota*), hop (e.g. *H. lupulus*), witch hazel (e.g. *Hamamelis*), oak (e.g. *Quercus*), Camellia (e.g. *Theacea*), red clover (e.g. *T. pratense*), flax (e.g. *L. usitatissiumum*), lemon (e.g. *C. limon*), birch (e.g. *Betula*), cornflower (e.g. *C. cyanus*), geranium, polygonum, soy (e.g. *G. max*), Sophora (e.g. *S. flavescens*), and combinations thereof, wherein the salicylic acid compound is present in an amount of from about 0.01% to about 10% (e.g. about 0.05% to about 5%, about 0.1% to about 3%) by weight of the composition, wherein the glycyrrhizic acid compound (e.g. MAG) is present in an amount of from about 0.01% to about 10% (e.g. about 0.01% to about 5%, about 0.05% to about 2%) by weight of the composition, and wherein the polyphenolic antioxidant agent is present in an amount of from about 0.0001% to about 10% (e.g. about 0.0001% to about 5%, about 0.001% to about 2%) by weight of the composition.

In one embodiment, the cosmetic composition of the invention comprises:
  (i) a salicylic acid compound comprising salicylic acid;
  (ii) a glycyrrhizic acid compound selected from the group consisting of monoammonium glycyrrhizate (MAG), triammonium glycyrrhizate, monopotassium glycyrrhizate, dipotassium glycyrrhizate, tripotassium glycyrrhizate, monosodium glycyrrhizate, disodium glycyrrhizate, trisodium glycyrrhizate, or combinations thereof (preferably MAG); and
  (iii) a polyphenolic antioxidant agent selected from the group consisting of extracts of: green tea (e.g. green leaves of *C. sinensis*), mulberry (e.g. *M. alba*), ginseng (e.g. *P. ginseng*), raspberry, oregano (e.g. *O. vulgare*), white tea (e.g. *C. sinensis*), red tea, Mohani tea, black tea, Oolong tea, yellow tea, jasmine tea, Pu Erh tea, blueberry (e.g. *V. cyanococcus*), French maritime pine bark (e.g. *P. pinaster*, sold under the trade name of Pycnogenol), rosemary (e.g. *R. officialis*), grape, including grape seed (e.g. *V. vinifera*), fennel (e.g. *F. fructus*), *C. sinica*, majaoram (e.g. *O. majorana*), crocus (e.g. *C. sativus*), apple (e.g. *M. domestica*), coffee, green coffee, cherry (e.g. *P. avium*), snow algae (e.g. *C. nivalis*), Emblica (e.g. *P. emblica*), ginkgo (e.g. *G. biloba*), moringa (e.g. *M. oleilera*), ginger, magnolia (e.g. *M. virginiana*), French saffron, edelweiss (e.g. *L. alpinium*), white lotus (e.g. *N. alba*), turmeric root, marshmallow (e.g. *A. officianlis*), burdock (e.g. *A. lappa*), bilberry (e.g. *V. myrtillus*), cranberry (e.g. *V. oxycoccus*), pomegranate (e.g. *P. granatum*), sage (e.g. *S. officianlis*), thyme (e.g. *T. vulgaris*), sunflower (e.g. *H. annus*), wild carrot (e.g. *D. carota*), hop (e.g. *H. lupulus*), witch hazel (e.g. *Hamamelis*), oak (e.g. *Quercus*), Camellia (e.g. *Theacea*), red clover (e.g. *T. pratense*), flax (e.g. *L. usitatissiumum*), lemon (e.g. *C. limon*), birch (e.g. *Betula*), cornflower (e.g. *C. cyanus*), geranium, polygonum, soy (e.g. *G. max*), Sophora (e.g. *S. flavescens*), and combinations thereof.

In one embodiment, the cosmetic composition of the invention comprises:
  (i) a salicylic acid compound comprising salicylic acid;
  (ii) a glycyrrhizic acid compound selected from the group consisting of monoammonium glycyrrhizate (MAG), triammonium glycyrrhizate, monopotassium glycyrrhizate, dipotassium glycyrrhizate, tripotassium glycyrrhizate, monosodium glycyrrhizate, disodium glycyrrhizate, trisodium glycyrrhizate, or combinations thereof (preferably MAG); and
  (iii) a polyphenolic antioxidant agent selected from the group consisting of extracts of: green tea (e.g. *C. sinensis*), ginkgo (e.g. *G. biloba*), Emblica (e.g. *P. emblica*), mulberry (e.g. *M. alba*), ginseng (e.g. *P. ginseng*), Sophora (e.g. *S. flavescens*), and combinations thereof.

In one embodiment, the cosmetic composition of the invention comprises:
  (i) a salicylic acid compound comprising salicylic acid;
  (ii) a glycyrrhizic acid compound selected from the group consisting of monoammonium glycyrrhizate (MAG), triammonium glycyrrhizate, monopotassium glycyrrhizate, dipotassium glycyrrhizate, tripotassium glycyrrhizate, monosodium glycyrrhizate, disodium glycyrrhizate, trisodium glycyrrhizate, or combinations thereof (preferably MAG); and
  (iii) a polyphenolic antioxidant agent selected from the group consisting of extracts of: green tea (e.g. green leaves of *C. sinensis*), white tea (e.g. *C. sinensis*), red tea, Mohani tea, black tea, Oolong tea, yellow tea, jasmine tea, Pu Erh tea, and combinations thereof.

In one embodiment, the cosmetic composition of the invention comprises: (i) a salicylic acid compound comprising salicylic acid; (ii) a glycyrrhizic acid compound comprising monoammonium glycyrrhizate (MAG); and (iii) a polyphenolic antioxidant agent comprising an extract of green tea. In one such embodiment, the cosmetic composition of the invention may comprise the salicylic acid in an amount of from about 0.01% to about 10% (e.g. about 0.05% to about 8%, about 0.1% to about 5%) by weight of the composition, the monoammonium glycyrrhizate in an amount of from about 0.01% to about 5% (e.g. about 0.01% to about 3%, about 0.05% to about 2%) by weight of the composition, and the extract of green tea in an amount of from about 0.0001% to about 10% (e.g. about 0.0001% to about 5%, about 0.001% to about 2%) by weight of the composition.

In one embodiment, the cosmetic composition of the invention comprises: (i) a salicylic acid compound; (ii) a glycyrrhizic acid compound (e.g. MAG); (iii) a polyphenolic antioxidant agent; and (iv) panthenol. In one such embodiment, the polyphenolic antioxidant agent may comprise an extract of green tea.

In one embodiment, the cosmetic composition of the invention comprises: (i) a salicylic acid compound; (ii) a glycyrrhizic acid compound (e.g. MAG); (iii) a polyphenolic antioxidant agent; and (iv) α-bisabolol. In one such embodiment, the polyphenolic antioxidant agent may comprise an extract of green tea.

In one embodiment, the cosmetic composition of the invention comprises: (i) a salicylic acid compound; (ii) a glycyrrhizic acid compound (e.g. MAG); (iii) a polyphenolic antioxidant agent; (iv) panthenol; and (v) α-bisabolol. In one such embodiment, the polyphenolic antioxidant agent may comprise an extract of green tea.

The cosmetic composition of the invention may comprise a cosmetically acceptable carrier.

The cosmetically acceptable carrier may be water-based, oil-or wax-based, or emulsion-based.

In embodiments where the carrier is emulsion-based, the composition may be in the form of a water-in-oil, an oil-in-water, a water-in-oil-in-water or an oil-in-water-in-oil emulsion.

In embodiments where the carrier is water-based, water may be present at a level of about 40% or more, about 45% or more, about 50% or more, about 55% or more, or about 60% or more by weight of the composition.

In embodiments where the carrier is oil-or wax-based, the oil and/or wax may be present at a level of about 15% or more, about 20% or more, about 30% or more, about 25% or more, about 35% or more, or about 40% or more by weight of the composition.

For example, in one embodiment the carrier may be water based and may comprise de-ionized water, purified water, natural spring water, rose water or the like. Mixtures of more than one of these may also be used. In one embodiment de-ionized or purified water is used.

The water based carrier may be 100% water or it may comprise components other than water. These may be components known for use in cosmetic formulations. They may include, but are not limited to, agents such as water-soluble moisturising agents, conditioning agents, anti-microbials, humectants (e.g. glycerin) and/or other water-soluble skin care actives.

In another embodiment, the carrier may be oil or wax based. The oil may be natural oil or synthetic oil, but preferably is natural oil such as a vegetable oil or a nut oil. The oil may be liquid or solid. The wax is preferably a natural wax.

Clearly the oil or wax that is chosen must be able to act as a carrier. Preferably it is a material that can easily be blended at room temperature; thus it may be a liquid at room temperature or a solid that is stirrable at room temperature.

Combinations of one or more oils and/or one or more waxes may be used.

Liquid oils that can be mentioned include avocado oil, Camellia oil, turtle bean oil, macadamia nut oil, corn oil, mink oil, olive oil, Canoga oil, egg yolk oil, sesame seed oil, Persic oil, wheatgerm oil, Camellia sasanqua oil, castor oil, linseed oil, safflower oil, sunflower oil, grapeseed oil, apricot oil, shea oil, sweet almond oil, cotton oil, evening primrose oil, palm oil, perilla oil, hazelnut oil, soybean oil, peanut oil, tea seed oil, kaya oil, rice bran oil, rapeseed oil, alfalfa oil, Chinese tung tree wood oil, Japanese tung tree wood oil, jojoba oil, germ oil, poppyseed oil, pumpkin oil, blackcurrant oil, millet oil, barley oil, quinoa oil, rye oil, candlenut oil, passionflower oil, musk rose oil, triglycerine, glyceryl trioctanoate, and glyceryl triisopalmitate.

Solid oils/fats that can be mentioned include cocoa butter, coconut butter, horse fat, hardened coconut oil, palm oil, beef tallow, mutton tallow, hardened beef tallow, palm kernel oil, lard, Japan wax kernel oil, hardened oil, Japan wax, shea butter, and hardened castor oil.

Waxes that can be mentioned include beeswax, candelilla wax, carnauba wax, lanolin, lanolin acetate, liquid lanolin, sugar cane wax, fatty acid isopropyl lanolin, hexyl laurate, reduced lanolin, jojoba wax, hard lanolin, polyoxyethylene (hereinafter referred to as POE), lanolin alcohol ether, POE lanolin alcohol acetate, lanolin fatty acid polyethylene glycol, and POE hydrogenated lanolin alcohol ether. In one embodiment the carrier is not lanolin based.

Ester oils that can be mentioned include C12-C15 alcohols benzoate, tridecyl salicylate, dibutyl adipate, isopropyl myristate, cetyl octoate, octyldodecil myristate, isopropyl palmitate, butyl stearate, hexyl laurate, myristyl myristate, decyloleate, hexyldecyl dimethyl octoate, cetyl lactate, myristyl lactate, lanolin acetate, isocetyl stearate, isocetyl iso-stearate, 12-hydroxy cholesteryl stearate, di-2-ethylhexylic acid ethyleneglycol, dipentaerythritol fatty acid ester, N-alkylglycol monoisostearate, neopentylglycol dicaprate, diisostearyl malate, glyceryl di-2-heptyl undecanate, tri-methylol propane tri-2-ethylhexyl acid, tri-methylol propane triisostearate, pentaerythritol tetra-2-ethylhexyl acid, glyceryl tri-2-ethyl-hexanoate, tri-methylol propane triisostearate, cetyl-2-ethylexanoate, 2-ethylhexyl-palmitate, glycerine trimyristate, glyceride tri-2-heptyl undecatoic acid, methyl ester of castor oil fatty acid, oleate oil, acetoglyceride, palmitate-2-heptyl undecyl, diisopropyl adipate, N-lauroyl-L-glutamic acid-2-octyldodecil ester, di-2-heptylundecyl adipate, di-2-ethylhexyl sebacate, myristate-2-hexyldecyl, palmitate-2-hexyldecyl, adipate-2-hexyldecyl, diisopropyl sebacate, and succinate-2-ethylhexyl.

Higher fatty acids that can be mentioned include lauric acid, myristic acid, palmitic acid, stearic acid, behenic acid, oleic acid, 12-hydroxy-stearic acid, undecylenic acid, lanolin fatty acid, isostearic acid, linoleic acid, linolenic acid, and eicosapentaenoic acid.

Higher alcohols of straight/branched chain that can be mentioned include lauryl alcohol, cetyl alcohol, stearyl alcohol, behenyl alcohol, myristyl alcohol, oleyl alcohol, cetostearyl alcohol, monostearyl glycerine ether (batyl alcohol), 2-decyltetradecinol, lanolin alcohol, cholesterol, phytosterol, hexyldodecanol, isostearyl alcohol, octyldodecanol.

The cosmetic composition of the invention may be provided in any form suitable for topical application to the skin. The cosmetic composition of the invention may be delivered and/or applied to the skin via any of the conventional formulations known to those skilled in the art. Typical formulation types of the present invention are creams, lotions, milks, gels, serum, foams, and ointments. In one embodiment, the cosmetic composition of the present invention is in the form of a cream or lotion.

The cosmetic composition of the invention will generally further comprise other ingredients or excipients which will be well known to those skilled in the art.

For example, the cosmetic composition of the invention may further comprise one or more humectants, including but not limited to glycerin, propylene glycol, propanediol, butylene glycol, pentylene glycol, hexylene glycol, hexanediol, dipropylene glycol, polyethylene glycol, sorbitol, sodium hyaluronate, urea, xylitol, lactitol, fructose, glucose, mannose, xylose, honey, pyrrolidone, and carboxylic acid and salts thereof. When present, the one or more humectants may be present in the cosmetic composition in an amount of about 0.01% to about 20% by weight of the composition, about 0.1% to about 10%, or about 0.5% to about 7% by weight of the composition.

The cosmetic composition of the invention may further comprise one or more emollients, including but not limited to PPG-15 stearyl ether, ethylhexyl stearate, cetyl dimethicone, octyldodecanol, PPG-20 methyl glucose ether, isopropyl myristate, isopropyl paltimate, isopropyl laurate, isodecyl laurate, isodecyl neopentanoate, isohexadecane, pentaerythrityl tetraisostearate, caprylic/capric triglyceride, canola oil, sunflower oil (*Helianthus annus*), olive oil (*Olea europea*), cottonseed oil (*Gossypium herbaceum*), jojoba oil (*Simmondsia chinensis*), shea butter (*Butyrospermum parkii*), cocoa butter (*Theobroma cacao*), cupuacu butter (*Theobroma grandiflorum*), avocado oil (*Persea gratissima*), liquid paraffin, dimethicone, phenyl trimethicone, cyclopentasiloxane, dimethiconol and petrolatum. When present, the one or more emollients may be present in the cosmetic composition in an amount of about 0.01% to about 20% by weight of the composition, about 0.1% to about 10%, or about 0.5% to about 7% by weight of the composition.

The cosmetic composition may further comprise one or more emulsifiers, including but not limited to steareth-2, steareth-21, steareth-10, ceteareth-5, ceteareth-20, cetearyl glucoside, oleth-10, glyceryl stearate, polyglycerol-3 oleate, polyglyceryl-3 methylglucose distearate, sodium stearate, PEG-12 oleate, PEG-2 stearate, PEG-12 stearate, PEG-100 stearate, cetyl alcohol, cetearyl alcohol, potassium cetyl phosphate, cetearyl olivate, sorbitan olivate, PEG-80 sorbitan, sorbitan oleate, and/or sorbitan palmitate. In one embodiment, the cosmetic composition of the invention does not comprise sulphates as emulsifiers. In embodiments where one or more emulsifiers are present in the cosmetic composition, the one or more emulsifiers may be present in an amount of about 0.1% to about 10% by weight of the composition, about 0.25% to about 7.5% by weight of the composition, or about 0.5% to about 5% by weight of the composition. In one embodiment where one or more emulsifiers are present in the cosmetic composition, the one or more emulsifiers are present in an amount of about 0.5% to about 5% by weight of the composition.

The cosmetic composition of the invention may further comprise one or more surfactants, including but not limited to, anionic surfactants (e.g. sodium lauryl sulphate, sodium laureth sulphate, ammonium laureth sulphate, disodium laureth sulfosuccinate and sodium C12-15 pareth-12 carboxylate), amphoteric/zwitterionic surfactants (e.g. cocamidopropyl betaine, sodium cocoamphoacetate and cocamidopropyl hydroxysultaine), non-ionic surfactants (e.g. cocamide DEA, cocamide MEA, decyl glucoside, lauryl glucoside), and cationic surfactants (e.g. cetrimonium chloride, behentrimonium chloride and benzalkonium chloride). In one embodiment, the cosmetic composition of the invention does not comprise sulphates as surfactants. In embodiments where one or more surfactants are present in the cosmetic composition, the one or more surfactants may be present in an amount of about 0.1% to about 10% by weight of the composition, about 0.25% to about 7.5% by weight of the composition, or about 0.5% to about 5% by weight of the composition. In one embodiment where one or more surfactants are present in the cosmetic composition, the one or more surfactants are present in an amount of about 0.5% to about 5% by weight of the composition.

The cosmetic composition of the invention may further comprise one or more preservatives, including but not limited to, 2-bromo-2nitropropane-1,3-diol (bronopol, commercially available under the trade name Myacide RTM), benzyl alcohol, benzoic acid, sodium benzoate, diazolidinyl urea, imidazolidinyl urea, methyl paraben, phenoxyethanol, ethyl paraben, propyl paraben, sodium methyl paraben, sodium dehydroacetate, dehydroacetic acid, polyhexamethylenebiguanide hydrochloride, isothiazolone, chlorhexidine digluconate, chlorphensin and/or sodium propyl paraben. In one embodiment, the cosmetic composition of the invention does not comprise parabens. In embodiments where one or more preservatives are present in the cosmetic composition, the one or more preservatives may be present in an amount of about 0.001% to about 10% by weight of the composition, about 0.01% to about 8% by weight of the composition, or about 0.1% to about 5% by weight of the composition. In one embodiment where one or more preservatives are present in the cosmetic composition, the one or more preservatives are present in an amount of about 0.05% to about 8% by weight of the composition.

The cosmetic composition of the invention may further comprise one or more chelating agents or sequestering agents, including but not limited to, ethylenediamine tetraacetic acid (EDTA) and salts thereof (e.g. dipotassium EDTA, disodium EDTA or tetrasodium EDTA), sodium phytate, trisodium ethylene diamine disuccinate, and/or tetrasodium glutamate diacetate. In embodiments where one or more chelating agents are present in the cosmetic composition, the one or more chelating agents may be present in an amount of about 0.001% to about 10% by weight of the composition, about 0.01% to about 8% by weight of the composition, or about 0.1% to about 5% by weight of the composition. In one embodiment where one or more chelating agents are present in the cosmetic composition, the one or more chelating agents are present in an amount of about 0.05% to about 8% by weight of the composition.

The cosmetic composition of the invention may further comprise one or more vitamins. For example, the cosmetic composition may further comprise vitamin B, vitamin B1 to vitamin B12, vitamin C, vitamin D, vitamin E, vitamin K, vitamin H, derivatives thereof, provitamins thereof (e.g. pro-vitamin B5 (panthenol)), or combinations thereof. In embodiments where one or more vitamins are present in the cosmetic composition, the one or more vitamins may be present in an amount of about 0.0001% to about 50% by weight of the composition, about 0.001% to about 10% by weight of the composition, about 0.01% to about 8% by weight of the composition, or about 0.1% to about 5% by weight of the composition. In one embodiment where one or more vitamins are present in the cosmetic composition, the one or more vitamins are present in an amount of about 0.1% to about 5% by weight of the composition. In one embodiment where one or more vitamins are present, the vitamin is vitamin C or a derivative thereof.

The cosmetic composition of the invention may further comprise one or more sunscreen agents, including but not limited to inorganic sunscreen agents (e.g. microfine titanium dioxide, microfine zinc oxide, iron oxides, talcs and/or boron nitride) and organic sunscreen agents (e.g. p-aminobenzoic acids, esters and derivatives thereof (e.g. 2-ethylhexyl p-dimethyl-aminobenzoate), methoxycinnamate esters (e.g. 2-ethylhexyl p-methoxycinnamate, 2-ethoxyethyl p-methoxycinnamate or β,β-di-(p-methoxycinnamoyl)-α'-(2ethylhexanoyl)-glycerin), benzophenones (e.g. oxybenzone), dibenzoylmethanes (e.g. 4-(tert-butyl)-4'-methoxydibenzoylmethane), 2-phenylbenzimidazole-5 sulfonic acid and salts thereof, alkyl-β,β-diphenylacrylates (e.g. alkyl α-cyano-β,β-diphenylacrylates such as octocrylene) triazines (such as 2,4,6-trianilino-(p-carbo-2-ethylhexyl-1-oxy)-1,3,5 triazine), and/or camphor derivatives (such as methylbenzylidene camphor). In embodiments where one or more sunscreen agents are present in the cosmetic composition, the one or more sunscreen agents may be present in an amount of about 0.01 to about 10% by weight of the composition.

The cosmetic composition of the invention may further comprise one or more pH adjusting agents, including but not limited to potassium hydroxide, sodium hydroxide, aminomethyl propanol, sodium citrate, and/or triethanolamine. The cosmetic composition of the invention may have a pH between about 3 and about 10, about 4 and about 8, or about 5 and about 7. In embodiments where one or more sunscreen agents are present in the cosmetic composition, the one or more sunscreen agents may be present in an amount of about 0.01 to about 10% by weight of the composition.

The cosmetic composition of the invention may further comprise one or more thickeners or gelling agents. For example, when the cosmetic composition is in the form of a gel, the cosmetic composition may comprise one or more thickeners or gelling agents. Examples of thickeners/gelling agents that can be used in the present invention include, but are not limited to, acrylic acid polymers (e.g. available commercially under the trade name Carbopol or Ultrez (Lubrizol), modified celluloses (e.g. hydroxyethylcellulose available commercially under the trade name Natrosol from Hercules) hydroxypropylmethyl cellulose, amine oxides, block polymers of ethylene oxide and propylene oxide (e.g. those available from BASF Wyandotte under the trade name "Pluronic"), PVM, MA, decadiene crosspolymer (e.g. available under the trade name Stabilez 60), ethoxylated fatty alcohols, salt (e.g. magnesium chloride, sodium chloride), Aristoflex AVC, phthalic acid amide, xanthan gum, sodium polyacrylate, polyvinyl alcohols, fatty alcohols, and/or alkyl galactmanans (e.g. available under the trade name N-Hance from Hercules. In embodiments where one or more thickeners/gelling agents are present in the cosmetic composition, the one or more thickeners/gelling agents may be present in an amount of about 0.01 to about 10% by weight of the composition.

The cosmetic compositions of the invention may further comprise one or more perfumes and/or colourings.

The cosmetic treatment may for alleviating or preventing the appearance of a skin condition selected from the group consisting of skin ageing, skin elastosis, skin laxity (sagging), rhytids (wrinkles), skin inflammation, skin damage, skin burn, skin pain, muscle tightness and acne.

In the present application, the term "about" may encompass ±10%, such as ±5%, e.g. ±2% or ±1%.

The skilled person will understand that optional features of one embodiment or aspect of the invention may be applicable, where appropriate, to other embodiments or aspects of the invention.

There now follows by way of example only a description of the present invention with reference to the accompanying drawings, in which:

FIG. 1 shows a list of example cosmetic compositions according to the invention.

FIG. 2 shows the percentage IL-6 inhibition in skin cells in the presence of either (a) a composition comprising $5\times10^{-4}$% w/w monoammonium glycyrrhizate (MAG) and $1\times10^{-3}$% w/w salicylic acid; (b) a composition comprising $5\times10^{-4}$% w/w MAG, $1\times10^{-3}$% w/w salicylic acid and $1\times10^{-6}$% green tea extract; (c) a composition comprising $1\times10^{-3}$% w/w MAG; (d) a composition comprising $1\times10^{-3}$% w/w salicylic acid and (e) a composition comprising $1\times10^{-4}$% green tea extract.

EXAMPLES

Embodiments of the invention will now be described in more detail, by way of example only.

Example 1—Interleukin-6 (IL-6) assay

Interleukin-6 (IL-6) bioactivity in skin cells was measured. IL-6 is a cytokine and used as a biomarker for inflammation. Skin cells (keratinocytes or fibroblasts) were placed under UV stress to induce an IL-6 response in the presence of anti-inflammatory agents or skin-soothing agents to determine their activity in inhibiting an IL-6 response.

Cells (keratinocytes or fibroblasts) were taken from culture, seeded in a 96-well plate at a density of 5000 cells per well in cell growth media with supplements and left to incubate for 24 hours at 37° C. Determination of cell number for the purpose of plating was performed in accordance with standard methods known in the art.

After incubation, the cell growth media was replaced with 100 μl of PBS without calcium and magnesium and containing the relevant concentration of agent(s) required. Dimethyl sulfoxide (DMSO) was used where necessary to dissolve the agent(s). Salicylic acid is the positive control for this assay.

The cells were incubated with the agents for 30 minutes at 37° C. before being irradiated with a UV dose of 61,500 Joules/m2. The concentration of agent used in the assay is 10 to 100-fold less than the concentration of agent typically present in a cosmetic composition because this assay involved direct application of the agents onto the cells compared to the indirect contact that takes place in vivo (this is known in the art).

After irradiation, the PBS and agents were replaced with 100 μl of pre-warmed (37° C.) media without supplements and incubated for 24 hours at 37° C.

Media supernatant containing the Il-6 expressed from the cells was then collected and transferred to a fresh 96-well plate and stored at −20° C. until the ELISA was performed.

The Il-6 ELISA was performed according to the manufacturer's protocol provided with the kit and as standard in the art.

A cell viability assay was performed on remaining cells where necessary to determine the cytotoxic effects of tested agents.

FIG. 2 shows that the percentage IL-6 inhibition in skin cells is surprisingly much greater in the presence of the combination of a salicylic acid compound (namely salicylic acid), a glycyrrhizic acid compound (namely monoammonium glycyrrhizate) and a polyphenolic antioxidant agent (namely green tea extract) (referred to herein as the "triple combination") when compared to the combination of MAG with salicylic acid, or MAG alone, or salicylic acid alone or green tea alone. Note here that the concentration of the green tea extract in the green tea extract alone result ($1\times10^{-4}$% w/w) is one hundred-fold greater than the concentration of the concentration of green tea extract used in the triple combination ($1\times10^{-6}$% w/w) and that the concentration of MAG in the MAG alone result ($1\times10^{-3}$% w/w) is double that of the concentration of MAG used in the triple combination ($5\times10^{-4}$% w/w), making the result of the triple combination even more surprising.

The invention claimed is:

1. A cosmetic composition comprising:
   (i) a salicylic acid compound comprising a compound chosen from salicylic acid, a salt of salicylic acid, benzyl salicylate, betaine salicylate, thiosalicylic acid, and salicylic acid esters;
   (ii) monoammonium glycyrrhizate; and
   (iii) a polyphenolic antioxidant agent;
   wherein the salicylic acid compound is present in an amount at least 10 times as much as the amount of polyphenolic antioxidant agent, and
   wherein the monoammonium glycyrrhizate is present in an amount at least 10 times as much as the amount of polyphenolic antioxidant agent.

2. The cosmetic composition of claim 1, wherein the salicylic acid compound is present in an amount of about 0.01% to about 5% by weight of the composition.

3. The cosmetic composition of claim 1, wherein the monoammonium glycyrrhizate is present in an amount of:
   (a) from about 0.001% to about 10% by weight of the composition;
   (b) from about 0.001% to about 5% by weight of the composition; or
   (c) from about 0.01% to about 3% by weight of the composition.

4. The cosmetic composition of claim 1, wherein the polyphenolic antioxidant agent is selected from the group consisting of extracts of: green tea, white tea, red tea, Mohani tea, black tea, Oolong tea, yellow tea, jasmine tea, Pu Erh tea, mulberry, ginseng, raspberry, oregano, blueberry, French maritime pine bark, grape, including grape seed, fennel, *Caragana sinica*, marjoram, crocus, apple, coffee, green coffee, cherry, snow algae, Emblica, Ginkgo, moringa, ginger, magnolia, French saffron, edelweiss, white lotus, turmeric root, marshmallow, burdock, bilberry, cranberry, pomegranate, sage, thyme, sunflower, wild carrot, hop, witch hazel, oak, Camellia, red clover, flax, lemon, birch, cornflower, geranium, polygonum, soy, Sophora, and combinations thereof.

5. The cosmetic composition of claim 4, wherein the polyphenolic antioxidant agent comprises an extract of green tea.

6. The cosmetic composition of claim 1, wherein the polyphenolic antioxidant agent is present in an amount of:
   (a) from about 0.0001% to about 10% by weight of the composition;
   (b) from about 0.0001% to about 5% by weight of the composition; or
   (c) from about 0.0005% to about 3% by weight of the composition.

7. The cosmetic composition of claim 1, wherein the composition further comprises panthenol and/or a-bisabolol.

8. The cosmetic composition of claim 1, wherein the salicylic acid compound, the monoammonium glycyrrhizate and the polyphenolic antioxidant agent are present in a total amount of:
   (a) from about 0.01% to about 20% by weight of the composition;
   (b) from about 0.05% to about 10% by weight of the composition; or
   (c) from about 0.05% to about 5% by weight of the composition.

9. A method of cosmetic treatment of a skin condition comprising the step of applying the cosmetic composition as defined in claim 1 onto the skin of a subject afflicted with the skin condition or a risk of being afflicted with the skin condition.

10. A method of cosmetically treating skin damage as a result of pollution insult, or of cosmetically preventing the detrimental effects of pollution to the skin, said method comprising applying an effective amount of the cosmetic composition as defined in claim 1 to the skin of a subject in need thereof.

* * * * *